(12) United States Patent
O'Lenick

(10) Patent No.: US 9,365,682 B2
(45) Date of Patent: Jun. 14, 2016

(54) SILICONE POLYMERS CONTAINING UV STABILIZING GROUPS

(71) Applicant: Thomas George O'Lenick, Dacula, GA (US)

(72) Inventor: Thomas George O'Lenick, Dacula, GA (US)

(73) Assignee: SurfaTech Corporation, Lawrenceville, GA (US)

(*) Notice: Subject to any disclaimer, the term of this patent is extended or adjusted under 35 U.S.C. 154(b) by 0 days.

(21) Appl. No.: 14/757,128

(22) Filed: Nov. 24, 2015

(65) Prior Publication Data

US 2016/0083525 A1    Mar. 24, 2016

Related U.S. Application Data

(60) Division of application No. 14/545,127, filed on Mar. 30, 2015, now Pat. No. 9,228,062, which is a continuation-in-part of application No. 14/120,763, filed on Jun. 25, 2014, now Pat. No. 9,045,593.

(60) Provisional application No. 61/967,745, filed on Mar. 26, 2014.

(51) Int. Cl.

| | | |
|---|---|---|
| *C08G 77/14* | (2006.01) |
| *C08G 77/388* | (2006.01) |
| *C07D 249/20* | (2006.01) |
| *C07D 251/54* | (2006.01) |
| *C08G 63/695* | (2006.01) |
| *C08G 77/04* | (2006.01) |
| *C08G 77/445* | (2006.01) |
| *C08G 77/16* | (2006.01) |
| *C08G 77/46* | (2006.01) |

(52) U.S. Cl.
CPC ........... *C08G 77/388* (2013.01); *C07D 249/20* (2013.01); *C07D 251/54* (2013.01); *C08G 63/695* (2013.01); *C08G 77/045* (2013.01); *C08G 77/14* (2013.01); *C08G 77/445* (2013.01); *C08G 77/16* (2013.01); *C08G 77/46* (2013.01)

(58) Field of Classification Search
CPC ........................... C08G 77/045; C07D 249/20
See application file for complete search history.

(56) References Cited

U.S. PATENT DOCUMENTS 5,102,707 A * 4/1992 Canivenc ............. C08G 77/388
                                                            428/44
7,915,330 B2    3/2011 Bonda et al.

* cited by examiner

*Primary Examiner* — Kuo-Liang Peng

(57) ABSTRACT

The present invention is directed to a series of silicone containing polymers that contain photostabilizers that act as photo stabilizers for Ultra Violet radiation. The polymers of the present invention are multi functional sun-screening additives that allow in addition to photostabilizing the active sunscreen agent found in sunscreens, additionally provide high levels of UV protection in a cosmetically elegant base. The compounds are made by the reaction of a benzatriazole compound and a methyl ester silicone compound.

4 Claims, No Drawings

SILICONE POLYMERS CONTAINING UV STABILIZING GROUPS

RELATED APPLICATIONS

This application is a divisional application of Ser. No. 14/545,127 filed Mar. 30, 2015 which is a continuation in part of U.S. Ser. No. 14/120,763 filed Jun. 25, 2014, now U.S. Pat. No. 9,045,593 issued Jun. 2, 2015, which in turn claims priority to and benefit of U.S. Provisional Application Nos. 61/967,745, filed Mar. 26, 2014, the disclosures of each of which are incorporated herein for all purposes.

FIELD OF THE INVENTION

The present invention is directed to a series of silicone containing polymers that contain photostabilizers that act as photo stabilizers for Ultra Violet radiation. The polymers of the present invention are multi functional sun screening additives that allow in addition to photostabilizing the active sunscreen agent found in sunscreens, additionally provide high levels of UV protection in a cosmetically elegant base. Specific benzotriazole compounds are reacted with methyl ester containing silicone compounds to make esters. The resulting products are polymers by virtue of having been reacted with polymeric silicone compounds and provide photostability, improve skin aesthetics and better water resistance in formulation.

BACKGROUND OF THE INVENTION

The formulation of a high performance sunscreen product requires many ingredients. Most important of which is the sunscreen active. Since sunscreens are considered by the Food and Drug Administration (FDA) as a drug, the actives that can be used are carefully regulated. Some of these materials do however experience photodegradation in formulation. It is the minimization of this type photodegradation issues that the present invention is directed.

Ultraviolet radiation from the sun or artificial sources can damage materials and/or coatings containing photoactive substances, such as photoactive polymers, pigments and dyes, by altering chemical bonds in the structure of the polymer, pigment, or dye. This photodegradation can lead to color fading, loss of gloss, and/or loss of physical and protective properties of a photodegradable or photoactive polymer or coating. Understandably, photostabilizing or photostabilization is the process or effect of preventing the photodegradation of photoactive substances. In particular, photostabilizing can be increasing the light fastness of a composition, preventing yellowing, or color formation, and delaying or preventing photochemical reactions that adversely affect photoactive substances.

One method to protect photoactive substances is through the use of UV filters; one class of materials particularly suited to act as a UV filters are naphthalate polyesters, for example those patented by this assignee. Naphthalate polyesters are suitable UV filters because they have very high extinction coefficients and subsequently low transmission of ultraviolet (UV) radiation. Additionally, the incorporation of naphthalates into polyester polymers increase the polymer's thermal and structural stability, decrease the polymer's gas permeability, and dramatically block the transmission of UV radiation through the polymer. The UV filtering and improved physical characteristics have led to the use of naphthalate polymers and blends in a wide range of applications including beverage and personal care product packaging, protective screening films, sail cloth fiber and as an additive stabilizer in sunscreens and cosmetics.

While efficiently absorbing UV radiation, naphthalates dissipate (emit) the absorbed energy through fluorescence. Fluorescence is a type of luminescence in which an atom or molecule emits radiation, i.e., a photon, in passing from a higher to a lower electron state, as described in my co-pending application Ser. No. 11/891,280 filed Aug. 9, 2007, herein incorporated by reference. The term is restricted to phenomena in which the time interval between absorption and emission energy is extremely short. This fluorescence can be a positive attribute in enabling the ready detection of naphthalate containing polymers or in the development of fluorescent coatings and inks. Alternatively, the high absorption of UV radiation can produce color formation or yellowing after exposure to UV light. Although this yellowing may not impact mechanical and physical properties of the polymer, it is generally undesirable. The fluorescence, color formation, or yellowing phenomena are of concern especially in packaging of products when the product's appearance is to be as close to its natural state as desired. For example, in the packaging of foods and beverages, if food or beverages were inside a poly(ethylene-2,6-naphthalene dicarboxylate) ("PEN") container they may appear unnaturally colored.

Quenching fluorescence eliminates or reduces photon emission by providing an alternative pathway for the excited state energy, such as radiative loss (heat), or intersystem crossing to an excited triplet state. Methods to quench fluorescence in PEN have been disclosed, for example see references cited in U.S. Pat. No. 6,001,952. These examples disclose the use of o-chlorophenol to quench PEN fluorescence in chloroform solutions. Dissolving PEN in a chloroform solution to disperse a fluorescence quencher, however, is not practical since the PEN must have a low molecular weight to dissolve in the chloroform solution and only very dilute PEN solutions can be prepared.

Other compounds used to quench naphthalate fluorescence include: benzotriazoles, cyanoacrylates, benzophenones, and benzoxazinones (JP Pat. No. 08225672); cyclic imino esters or quinoxalines (EP Pat. No. 0711803); and benzylidene compounds (U.S. Pat. Nos. 4,617,374, 4,707,537, and 6,001, 952). Many of these examples are disadvantageous because they require postproduction coating of fluorescent materials, show inadequate reduction in the fluorescence from fluorescent materials, or are only effective in very dilute solutions. Accordingly, there is a need for naphthalate compositions having a reduced fluorescence without deleteriously affecting the physical properties of the polymer.

The absorption of ultraviolet light by a chromophore-containing organic molecule causes the excitation of an electron in the chromophore moiety from an initially occupied, low energy orbital to a higher energy, previously unoccupied orbital. The energy of the absorbed photon is used to energize an electron and cause it to "jump" to a higher energy orbital, see Turro, Modern Molecular Photochemistry, 1991. Two excited electronic states derive from the electronic orbital configuration produced by UV light absorption. In one state, the electron spins are paired (antiparallel) and in the other state the electron spins are unpaired (parallel). The state with paired spins has no resultant spin magnetic moment, but the state with unpaired spins possesses a net spin magnetic moment. A state with paired spins remains a single state in the presence of a magnetic field, and is termed a singlet state. A state with unpaired spins interacts with a magnetic field and splits into three quantized states, and is termed a triplet state.

In the electronically excited state, the chromophore-containing organic molecule is prone to degrade via a number of known pathways and, therefore, can absorb little or no additional UV light. To photostabilize an electronically excited chromophore-containing organic molecule in order to provide sufficient UV protection, it must be returned to the ground state before it undergoes a photochemical reaction destructive to its UV absorbing capability. There are known photostabilizing sunscreen additives, such as Octocrylene, methylbenzilydene camphor, and the esters or polyesters of naphthalene dicarboxylic acid of this assignee's U.S. Pat. Nos. 6,113,931; 6,284,916; 6,518,451; and 6,551,605, all hereby incorporated by reference, that are capable of quenching excited triplet state energy. Alkoxy crylenes, particularly methoxy crylenes, return chromophore-containing organic molecules, particularly butyl methoxydibenzoylmethane (Avobenzone), octyl methoxycinnamate (Octinoxate), and octyl salicylate (Octisalate), from both an electronically excited singlet state and excited triplet state back to their ground state, thereby photostabilizing the UV-absorbing organic molecules.

A compound known to those skilled in the art is iscotrizinol. This material sold under the trade name Unasorb ET by 3V Sigma, has the following structure and identifiers.

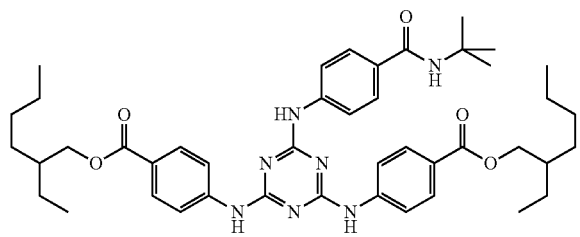 [SMILES: CCCCC(CC)COC(=O)c1ccc(Nc2nc(Nc3ccc(C(=O)NC(C)(C)C)cc3)nc(Nc3ccc(C(=O)OCC(CC)CCCC)cc3)n2)cc1]

The product has the following properties reported by 3V Sigma the manufacturer.

| Chemical and Physical Characteristics | |
|---|---|
| INCI Name: | Ethylhexyl Triazone |
| IUPAC Name: | 4,4'-[[6-[[4-[[(1,1-dimethylethyl)amino]-carbonyl]phenyl]amino]-1,3,5-triazine-2,4-diyl]diimino]bis-, bis(2-ethylhexyl)benzoate |
| CAS Number: | 154702-15-5 |
| Empirical Formula: | $C_{48}H_{66}N_6O_6$ |
| Molecular Weight: | 823.0 |
| Appearance: | Whitish Powder |
| Melt Point: | <132.0 |
| Specific Extinction: (at 314 nm in Ethanol) | |
| | Solubility (% w/w at 25° C.) |
| PEG-7 Glyceryl Cocoate: | ca. 10 |
| Diisopropyl Adipate: | ca. 9 |
| C12-15 Alkyl Benzoate: | ca. 4 |
| Caprylic/Capric Triglyceride: | ca. 4 |
| Isopropyl Palmitate: | ca. 2 |
| Mineral Oil: | <1 |

The referenced works establish the long felt need for photostabilizing polymers that are both efficient and effective. The need is primarily in the region of UVA. It is to this area that the current invention is directed. The specific polymers of the present invention result in products, which not only ameliorate the inherent photo instability, but also form films on the surfaces to which they are applied which are water resistant and stay in place increasing effectiveness and efficiency.

All references cited are incorporated herein by reference.

THE INVENTION

Object of the Invention

The present invention has as its object a series of silicone polymers that contain two specific benzotriazole ultraviolet photostabilizing moieties that are used to enhance the photostability of sunscreen formulations, specifically in the UVA region of the sunscreen spectrum.

Additionally, another object of the present invention is to provide specific polymers for use in sun screening applications.

Still another object of the present invention provides a process for protecting skin from the deleterious effects of the sun which comprises contacting the skin with an effective sun screening concentration of a polymer, which is produced using the current invention.

Other objects of the invention will become clear as one reads and understands the disclosure of the present invention.

All temperatures given are in degrees C., all percentages are percentages by weight and all references are incorporated herein by reference as allowed.

SUMMARY OF THE INVENTION

The present invention discloses a series of silicone polymers that contain two specific benzotriazole ultraviolet photostabilizing group that can be used to enhance the photostability of sunscreen formulations, specifically in the UVA region of the sunscreen spectrum.

One starting raw material has the following structure:

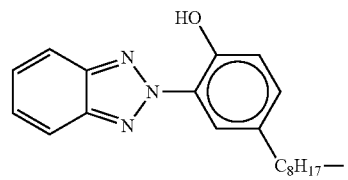

It is described as benzotriazole Ultraviolet Light Absorber, having the chemical name 2-(2-hydroxy-5-tert-octylphenyl) benzotriazole. It has the formula of $C_{20}H_{25}N_3O$ and the CAS number of 3147-75-9.

The second starting raw material has the following structure:

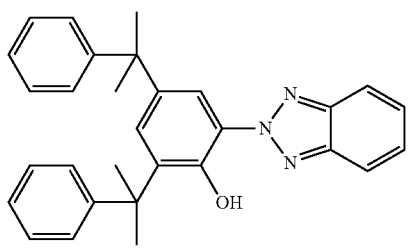

It is described as a benzotriazole Ultraviolet Light Absorber. It has the chemical name 2-[2-hydroxy-3,5-di-(1,1-dimethylbenzyl)]-2H-benzotriazole, the formula $C_{30}H_{29}N_3O$. The CAS number is 70321-86-7. It is available from Mayzo Inc is Swaunee Ga. as BLS 234.

The OH group on the compounds are reacted with specific silicone compounds. The silicones suitable for the synthesis of esters of the starting materials are selected from the group consisting of:

(i)
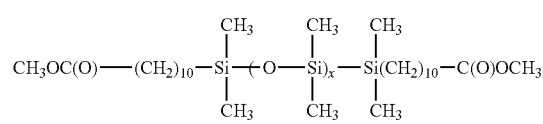

wherein x is an integer from 0 to 10;

(ii)
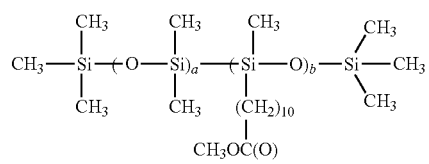

wherein:
a is an integer ranging from 0 to 20;
b is an integer ranging from 1 to 10.

The esters have one the following structures:

(i)
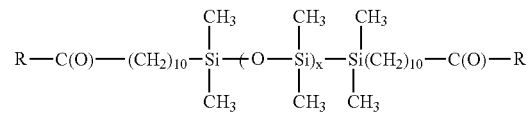

wherein x is an integer from 0 to 20;

(ii)
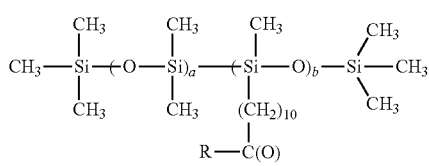

wherein
R is selected from the group consisting of:

(i)
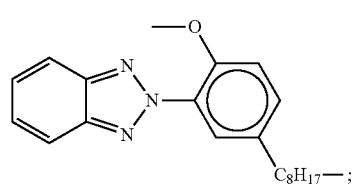

(ii)
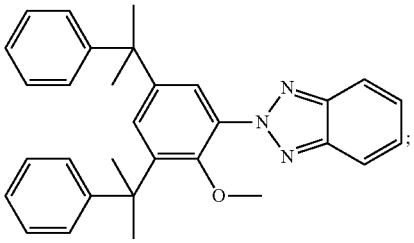

and
(iii)
mixtures thereof.

PREFERRED EMBODIMENTS

In a preferred embodiment R is

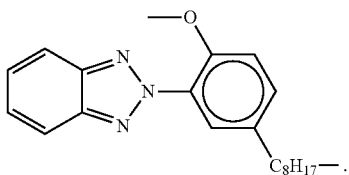

In a preferred embodiment R is

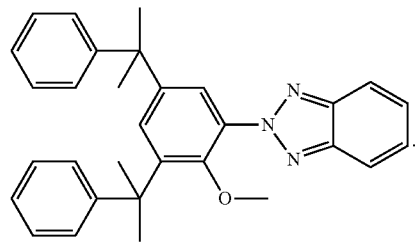

In a more preferred embodiment R is a mixture of;

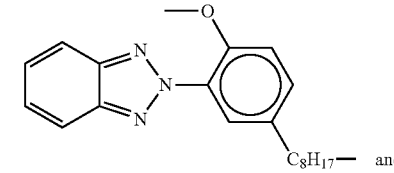 and

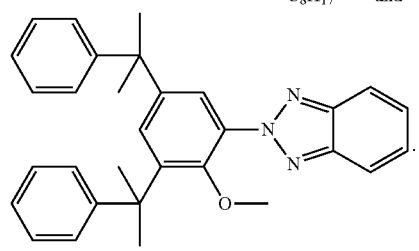

In a preferred embodiment x is 1.
In a preferred embodiment x is 2.
In a preferred embodiment x is 5.
In a preferred embodiment x is 10.

In a preferred embodiment x is 0.
In a preferred embodiment x is 20.
In a preferred embodiment a is 0.
In a preferred embodiment a is 5.
In a preferred embodiment a is 10.
In a preferred embodiment a is 15.
In a preferred embodiment a is 20.
In a preferred embodiment b is 1.
In a preferred embodiment b is 5.
In a preferred embodiment b is 10.
In a preferred embodiment b is 15.
In a preferred embodiment b is 20.

Raw Materials

Example 1

Benzenetriazole 1

Benzenetriazole 1 has the following structure;

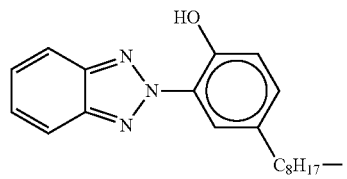

It is described as benzotriazole Ultraviolet Light Absorber, having the chemical name 2-(2-hydroxy-5-tert-octylphenyl) benzotriazole. It has the formula of $C_{20}H_{25}N_3O$ and the CAS number of 3147-75-9. It is available from Mayzo Inc of Swaunee Ga. as BLS 5411.

Example 2

Benzenetriazole #2

Benzenetriazole 2 has the following structure;

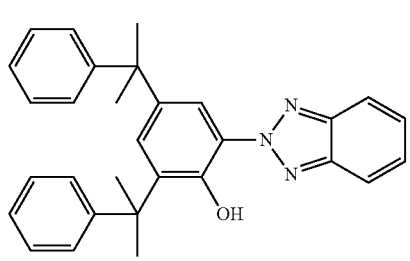 [SMILES: CC(C)(c1ccccc1)c1cc(-n2nc3ccccc3n2)c(O)c(C(C)(C)c2ccccc2)c1]

It is described as a benzotriazole Ultraviolet Light Absorber. It has the chemical name 2-[2-hydroxy-3,5-di-(1, 1-dimethylbenzyl)]-2H-benzotriazole, the formula $C_{30}H_{29}N_3O$. The CAS number is 70321-86-7. It is available from Mayzo Inc is Swaunee Ga. as BLS 234.

Silicone Polymers

One class of silicone polymers useful as raw materials in the preparation of the polyesters have the following structure:

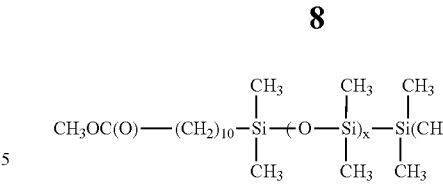

wherein x is an integer from 0 to 10;

These materials are items of commercially available from Siltech LLC, Lawrenceville Ga. under the trade name Silmer UME.

| Examples | x |
|---|---|
| 3 | 0 |
| 4 | 1 |
| 5 | 2 |
| 6 | 5 |
| 7 | 10 |
| 8 | 20 |

The second class of silicone polymers useful as raw materials in the preparation of the polyesters have the following structure:

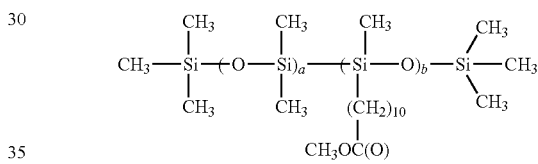

wherein:

a is an integer ranging from 0 to 20;

b is an integer ranging from 1 to 10.

These materials are items of commercially available from Siltech LLC, Lawrenceville Ga. under the trade name Silmer UME.

| Example | a | b |
|---|---|---|
| 9 | 0 | 1 |
| 10 | 5 | 10 |
| 11 | 10 | 5 |
| 12 | 15 | 15 |
| 13 | 20 | 20 |
| 14 | 0 | 20 |
| 15 | 20 | 1 |

Polymers of the Present Invention

General Procedure

In a suitable reaction flask capable of heating the contents to 200° C. is added the specified number of grams of the specified Benzenetriazole (Example 1 or 2), the specified number of grams silicone (Examples 3-15). The reaction is heated to 170-180° C. During the heating time and once the reaction reaches around 140° C. methanol begins to distill off. The temperature if held between 170 and 180° C. for 5 hours, then the reaction is followed by acid value, which drops during the reaction then stabilizes.

| | Benzenetriazole | | Silicone | |
|---|---|---|---|---|
| Example | Example | Grams | Example | Grams |
| 16 | 1 | 323 | 3 | 280 |
| 17 | 2 | 447 | 4 | 317 |
| 18 | 1 | 323 | 5 | 354 |
| 19 | 2 | 442 | 6 | 465 |
| 20 | 2 | 323 | 7 | 650 |
| 21 | 1 | 442 | 8 | 1020 |
| 22 | 2 | 447 | 9 | 437 |
| 23 | 1 | 323 | 10 | 326 |
| 24 | 2 | 447 | 11 | 453 |
| 25 | 1 | 323 | 12 | 358 |
| 26 | 2 | 447 | 13 | 355 |
| 27 | 1 | 323 | 14 | 281 |
| 28 | 2 | 447 | 15 | 1917 |
| 29 | 1 | 161.5 | 15 | 1917 |
| | 2 | 223.5 | | |

The compounds are used without purification.

The compounds of the present invention photostabilize sunscreens when added to sun screen formulations at a concentration of between 1 and 10% by weight.

Example 29 has both the benzatriazole compounds present. It provides the best photostability.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

I claim:
1. An ester having the following structure:

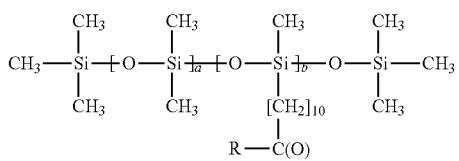

wherein
a is an integer ranging from 0 to 20;
b is an integer ranging from 1 to 10;
R is selected from the group consisting of:

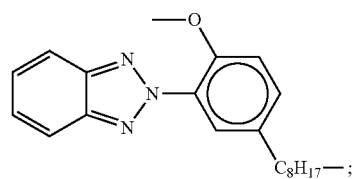

(i)

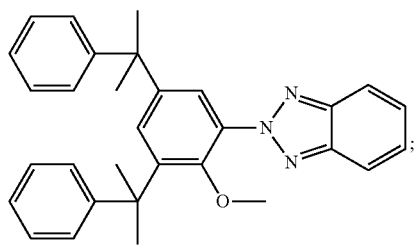 [SMILES: COc1c(-n2nc3ccccc3n2)cc(C(C)(C)c2ccccc2)cc1C(C)(C)c1ccccc1]

(ii)

and
(iii)
mixtures thereof.

2. The ester of claim 1 wherein a is 0.
3. The ester of claim 1 wherein a is 5.
4. The ester of claim 1 wherein a is 20.

* * * * *